United States Patent
Hansen

(10) Patent No.: US 8,361,141 B2
(45) Date of Patent: Jan. 29, 2013

(54) MODULAR STENT ASSEMBLY

(75) Inventor: Palle Munk Hansen, Bjaeverskov (DK)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 12/755,808

(22) Filed: Apr. 7, 2010

(65) Prior Publication Data

US 2010/0256741 A1    Oct. 7, 2010

(30) Foreign Application Priority Data

Apr. 7, 2009 (GB) .................................. 0906061.7

(51) Int. Cl.
*A61F 2/82* (2006.01)

(52) U.S. Cl. ....................................................... 623/1.16

(58) Field of Classification Search .................. None
See application file for complete search history.

(56) References Cited

U.S. PATENT DOCUMENTS

| | | | |
|---|---|---|---|
| 2002/0111671 A1 | 8/2002 | Stenzel | |
| 2002/0120327 A1 | 8/2002 | Cox et al. | |
| 2006/0173529 A1* | 8/2006 | Blank | 623/1.16 |
| 2006/0287706 A1 | 12/2006 | Olsen et al. | |
| 2007/0219613 A1 | 9/2007 | Kao et al. | |
| 2008/0195190 A1* | 8/2008 | Bland et al. | 623/1.11 |
| 2009/0005848 A1* | 1/2009 | Strauss et al. | 623/1.2 |

FOREIGN PATENT DOCUMENTS

| | | |
|---|---|---|
| EP | 1523960 | 4/2005 |
| WO | 0015151 | 3/2000 |
| WO | 03075797 | 9/2003 |
| WO | 2004110312 | 12/2004 |
| WO | 2005032414 | 4/2005 |
| WO | 2005067816 A1 | 7/2005 |
| WO | 2006010636 A1 | 2/2006 |
| WO | 2006089739 | 8/2006 |
| WO | PCT/US2010/030227 | 7/2010 |

* cited by examiner

*Primary Examiner* — Thomas J Sweet
*Assistant Examiner* — Rebecca Preston
(74) *Attorney, Agent, or Firm* — Brinks Hofer Gilson & Lione

(57) ABSTRACT

A modular stent assembly (20) is provided with stent sections (22-26) which are coupled together by a coupling arrangement formed of first (30) and second (32) coupling elements. The first and second coupling elements (30, 32) provide a strong coupling between adjacent stent sections (22-26) which behaves in a manner substantially identical to the conventional unitary tie bar. The modular nature of the stent assembly (20) reduces manufacturing costs, can provide for replacement of only a defective part of the assembly 20 and can facilitate the assembly of a stent having differing characteristics along its length optimised for a particular medical application.

13 Claims, 8 Drawing Sheets

MODULAR STENT ASSEMBLY

TECHNICAL FIELD

The present invention relates to a modular stent assembly for the production of stents, stent grafts, vena cava filters, occlusion devices and any other implantable medical device which includes a stent structure.

BACKGROUND ART

Stents have been known and in use for several decades. Some early types of stent were formed from wire of stainless steel or, more recently, of Nitinol or other shape memory material. The wire is formed into a series of rings, in which typically the wire of each ring has a curved or substantially zigzag shape to enable this to be compressed onto an introducer and to give the ring an adjustable radial dimension for a good fit into the lumen into which the stent is in use positioned. The rings are connected together to form a unitary structure by sets of tie bars. In such early types of stents, the coupling of the tie bars to the wire rings has been by any suitable bonding such as welding.

While such a stent structure can perform satisfactorily, the stent has reduced compressibility and expansion characteristics which, moreover, cannot be finely predicted or adjusted. This can lead to their unsuitability in some more delicate applications, such as in smaller and more delicate vessels including, for instance, cerebral vessels.

More recently, there have been provided stents which are formed from a tube of raw material in which the stent structure is laser cut from the tube. The Applicant's Zilver® Stent is an example of such a laser cut stent. The advantage of such a stent structure is that it has greater uniformity in its characteristics, greater compressibility and much greater predictability in its performance. For instance, the individual stent rings can compress much tighter than an equivalent ring formed from wire, as adjacent struts of the stent ring are formed by cutting rather than bending of a wire. Moreover, the stent structure can be designed to have accurate and reproducible flexibility and also to have a varying flexibility as desired, for instance by cutting the stent rings or the struts forming these to different or varying widths or thicknesses.

Whilst laser cut stents can have significantly superior performance characteristics, they are expensive to manufacture particularly when produced from expensive materials such as Nitinol, in that the procedure is time consuming and there is a large wastage of material. Moreover, the laser cutting operation is complex particularly given that it generally needs to be adaptable so as to be able to produce different stents, with different dimensions and characteristics in dependence upon the specific medical application to which they are to be used. In addition to these difficulties, should there be any defects in the stent, such as a defect occurring during manufacture or during subsequent handling of the stent, the entire stent must be discarded.

There are known various types of modular stent assemblies, disclosed for example in WO-2004/110312, U.S.-2002/0111671, WO-00/15151 and U.S.-2006/0173529. Generally, these modular assemblies are intended to give the stent structure different characteristics in different operating conditions, such as to be radially flexible when compressed onto an introducer and then to become radially stiffer when expanded and in situ in a patient.

DISCLOSURE OF THE INVENTION

The present invention seeks to provide an improved stent structure and in particular a modular stent assembly and components for forming a stent structure.

According to an aspect of the present invention, there is provided a stent assembly able to be conformed into a plurality of configurations including a compressed and an expanded configuration, the stent assembly including a plurality of stent sections, each stent section being provided with at least one set of coupling elements, wherein the coupling elements of at least two of said stent sections have co-operating forms so as to lock together in a substantially fixed manner in all configurations of the stent assembly.

Preferably, said co-operating coupling elements are of a form to snap-fit together.

By locking together in a substantially fixed manner, it is intended to mean that the coupling of the stent sections to one another is mechanically and behaviourally equivalent to a stent formed as a unitary structure, in particular in a manner similar to stent sections which are cut from a raw tubing.

Such a modular structure has a number of advantages. The manufacture of a stent can be substantially simplified in that the elements which are, preferably, laser cut are substantially smaller than a complete stent and can be manufactured in bulk in identical form. The stent can then be assembled by, in the preferred embodiment, snap-fitting however many sections together as is needed to meet the particular requirements for the medical application in question. Variations to the characteristics of the stent can be achieved by manufacturing different types of stent sections, for example of different flexibilities and the like, and then fitting different sections together to form a unitary structure with different characteristics. For instance, if it is desired to have a stent with a stiffer central part, stent sections with thicker elements or struts can be used for the central section, fitted to stent sections with thinner elements or struts at the ends of the stent assembly.

This modular form of stent assembly can also allow stents of any desired length to be produced, for instance by coupling together however many stent sections are necessary to achieve the desired length. It is not necessary to manufacture a specific stent of that length.

Furthermore, if a stent section is defective, it is not necessary to discard the entirety of a stent but only the defective section. There is therefore much less wastage of good stent material and avoidance of loss of a prepared stent for a medical application.

The assembly of the components of the stent would typically be carried out at the manufacturing facility upon the specific order of a customer but it is not excluded that such assembly could be carried out in situ by the clinical staff.

Preferably, the coupling elements of a set provide fixing of the two stent sections thereof both in a radial direction of the stent sections and in their longitudinal direction. By radial direction it is intended to mean a direction extending radially outwardly from a centre point of the stent sections, while by longitudinally it is intended to mean along an axis extending from one stent section to the other when assembled together. With such a coupling arrangement, two adjacent stent sections which are coupled together are fixed relative to one another in the principal directions of stent movement and thus provide a fixed coupling which behaves in a manner analogous to a unitary stent structure. In the preferred embodiment, the set of coupling elements provides a fixing in all directions of stent movement.

There are various examples of coupling arrangements disclosed below. The preferred coupling arrangement provides a first coupling member which has a generally round head with straightened sides and a corresponding second coupling element. Most preferably, the straightened sides taper towards one another in a radially internal direction of the stent section carrying the first coupling element. Advantageously, an innermost side of the first coupling section is provided with side extending flanges or feet. These side extending flanges or feet can be produced by cutting the rounded head only part-way through its thickness, so as to leave the feet as non-cut portions of the rounded head.

Advantageously, the rounded head is curved in the circumferential direction of the stent section, preferably with a radial curvature which substantially matches the radial curvature of the stent assembly when deployed.

This structure of coupling elements provides a snap-fit connection which is secure and which fixes two associated coupling elements in all directions of movement of the stent sections. The side extending feet and tapering nature of the straightened side walls ensure that the coupling cannot be uncoupled unintentionally.

In practice, the side extending feet will project into the inner lumen of the stent assembly. However, as these are relatively flat and rounded at their edges, they have been found to produce no significant effect on the characteristics of the stent assembly in comparison to conventional unitary stent assemblies.

According to another aspect of the present invention, there is provided a kit including plurality of stent sections for forming a stent assembly, which stent sections are able to be conformed into a plurality of configurations including a compressed and an expanded configuration, each stent section being provided with at least one set of coupling elements, wherein the coupling elements of at least two of said stent sections have co-operating forms so as to lock together in a substantially fixed manner in all configurations of the stent assembly.

According to another aspect of the present invention, there is provided a method of forming a stent or other stented medical device including the steps of snap fitting together a plurality of stent sections as specified herein to form a stented structure.

Even though the above and the specific description which follows focuses upon a stent, the teachings herein are applicable to any structure which uses or includes a stent support element, such as but not limited to stent grafts, occlusion devices, vena cava filters, and other similar implantable medical devices.

BRIEF DESCRIPTION OF THE DRAWINGS

Embodiments of the present invention are described below, by way of example only, with reference to the accompanying drawings, in which.

BEST MODE FOR CARRYING OUT THE INVENTION

Figure 1:
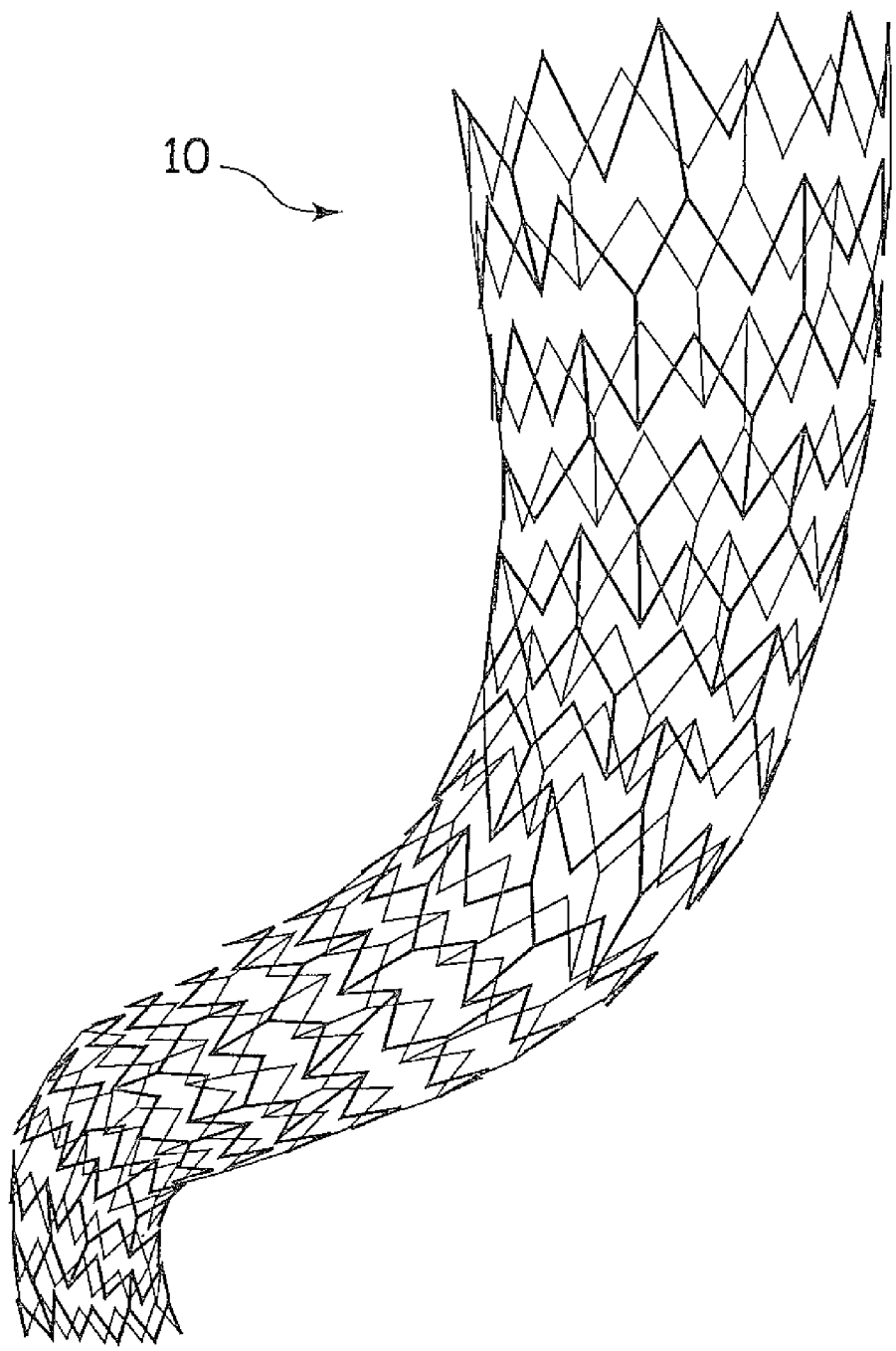
FIG. 1 is a perspective view of the applicant's Zilver® Stent.

Referring to FIG. 1, there is shown an example of the applicant's Zilver® Stent 10. This stent is formed by laser cutting a tube of Nitinol into the form shown in the Figure, that is into a plurality of zigzag stent rings connected to one another by a series of integral tie bars. This stent has particularly good physical characteristics as well as compressibility. However, as explained above, since the structure is unitary, it is expensive to manufacture and the entire stent 10 must be discarded if even a part of it is defective.

Figure 2:
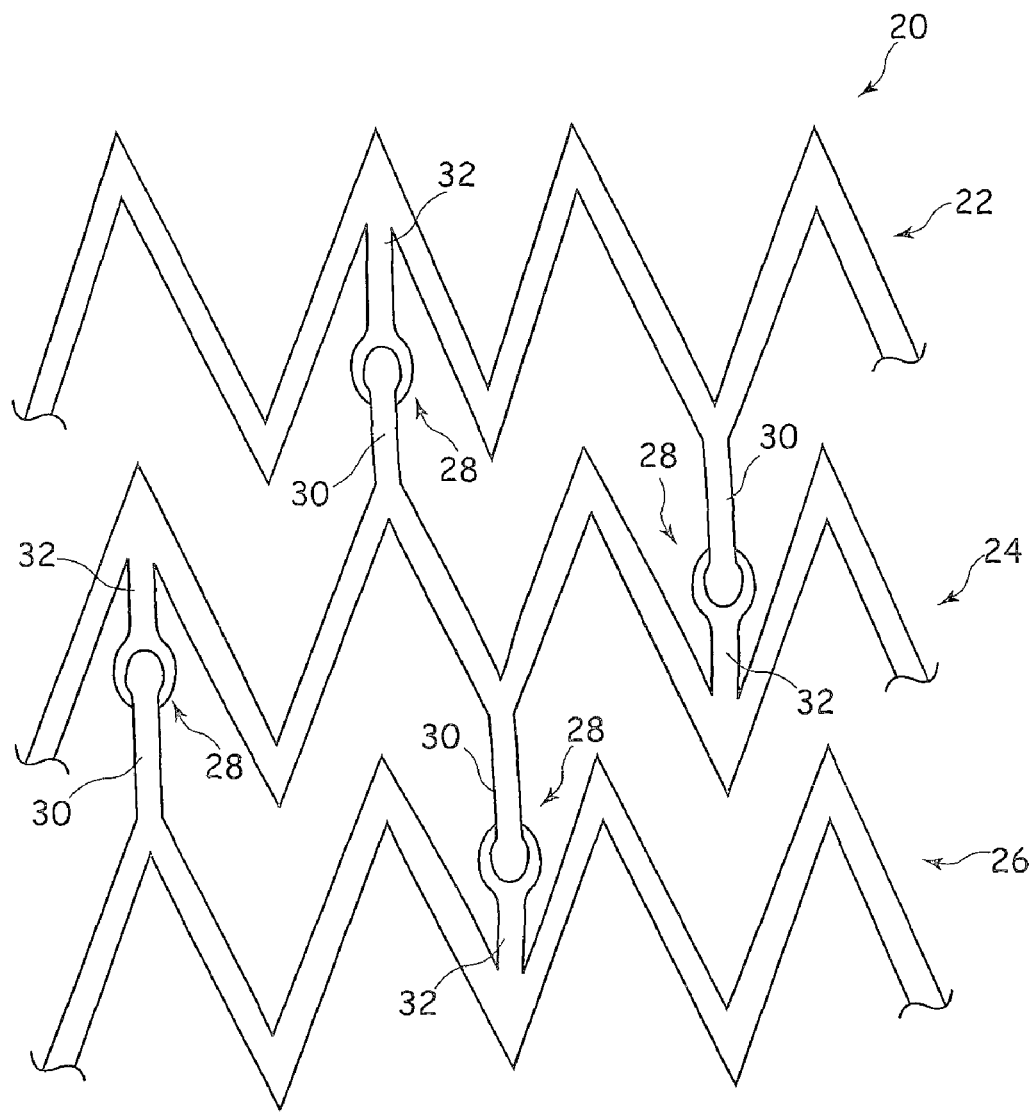
FIG. 2 is a schematic diagram of a part of a stent assembly according to one embodiment of the invention.

Referring now to FIG. 2, there is shown in schematic form a part of an embodiment of stent assembly 20 formed of a plurality of stent rings or sections 22, 24, 26 which are coupled to one another. FIG. 2 shows only three stent rings 22, 24, 26, although in practice there would typically be more than this, from 5 to 20 being a typical number. The actual number will be dependent upon the dimensions of the stent rings 22, 24, 26 and the overall desired length of the stent assembly 20 required for the particular medical application. In practice, the only limit to the number of stent rings will be related to the desired or necessary length of the stent assembly 20.

Each stent ring 22, 24, 26 is provided with parts coupling elements 30,32 which are positioned and selected to co-operate with corresponding coupling elements 30,32 of the immediately adjacent stent ring 22, 24, 26, such that adjacent stent rings 22, 24, 26 are fixed to one another by the sets 28 of coupling elements.

As will be described below in detail, the preferred embodiment provides first 30 and second 32 coupling elements. In the view of FIG. 2, each stent ring is provided with a regular mix of first and second coupling elements 30, 32, arranged in such a manner that a stent ring 24 can be used with other identical stent rings 24 to produce an assembly of any desired number of stent rings. In this embodiments, the stent rings 22 and 26 are end rings which differ from the ring 24 in having coupling elements only on an interior side of the ring. It will be appreciated that the rings 22 and 26 could be identical to the ring 24 in some instances and could, in addition or instead, be provided with one or more radio opaque markers of known form.

It is also envisaged that the stent ring 24 could be provided extending in one direction (for example upwardly in the view of FIG. 2) with only one type of the first and second coupling elements 30,32, there being provided the complementary coupling elements 32,30 extending in the other direction. This would also enable the stent ring 24 to couple to identical rings 24. In other embodiments, there may be a stent ring provided with only first coupling elements 30 and another type of stent ring provided only with second coupling elements 32. The arrangement of coupling elements is not critical to the performance of the stent assembly 20.

It will be appreciated from FIG. 2 that the coupling elements of this embodiment form the tie bars between two stent rings 22, 24, 26. This is the preferred arrangement as the stent rings 22, 24, 26 can thus be formed with unitary struts. However, it is also envisaged that one might wish to have the couplings within the struts of a strut ring rather than in the tie bars between strut rings.

Figure 3:
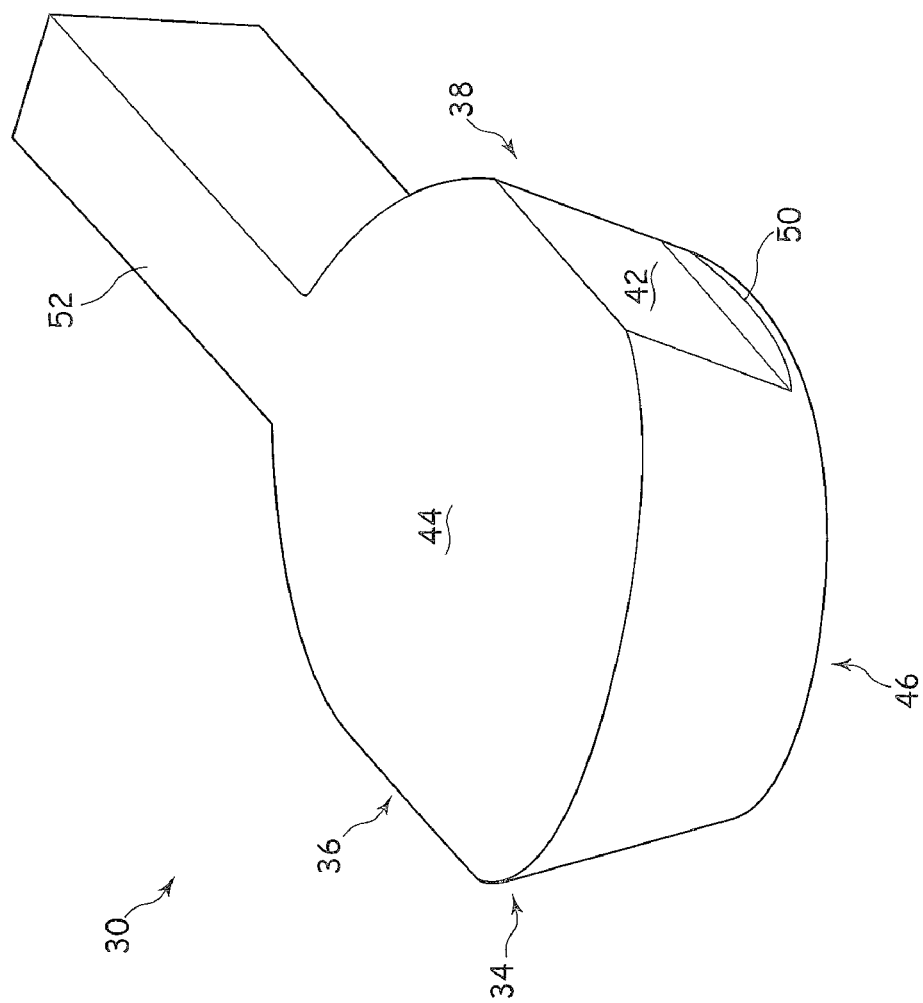
FIG. 3 is a perspective view of the preferred embodiment of first coupling element.

Referring now to FIG. 3, there is shown a perspective view from above of the preferred embodiment of first coupling element 30. This has an enlarged head 34 which curves in a radial direction of the strut rings and at a radius of curvature which preferably approximates the curvature of the stent 20 in its deployed configuration.

When seen from below, the enlarged head 34 is, in this embodiment, substantially round. It is also substantially round when seen from above, apart from at the two side sections 36,38, at which the enlarged head has been cut away to provide two substantially flat side walls 40, (shown more clearly in FIG. 6) 42 which are formed so as to extend inwardly from the top 44 of the enlarged head 34 towards its bottom 46. Thus, the two side walls 40, 42 extend towards one another from the top wall 44 to the bottom wall 46.

It is preferred that the two side walls 40,42 are substantially parallel to one another in a direction along the coupling element 30 and in particular with respect to the bar element 52. This could be described, in the embodiment shown, as the longitudinal direction of the stent 20.

The side walls 40, 42 end just before the bottom surface 46, so as to leave two side extending feet 48, (shown more clearly in FIG. 6) 50 extending along the bottom surface 46. The upper surfaces of the two feet 48, 50 are, in this embodiment, substantially parallel to the bottom surfaces of the feet at the wall 46 of the enlarged head. As can be seen in FIG. 3, the upper surfaces of the feet 48, 50 thus have a straight side, common with the ends of the flat walls 40,42 and opposite to these have curved sides, which will be part-circular.

The enlarged head 34 is integral with a bar element 52, which in this embodiment is in the form of a part tie-bar. The top and bottom surfaces of the bar element 52 preferably follows the curvature of the enlarged head 34.

Figure 4:
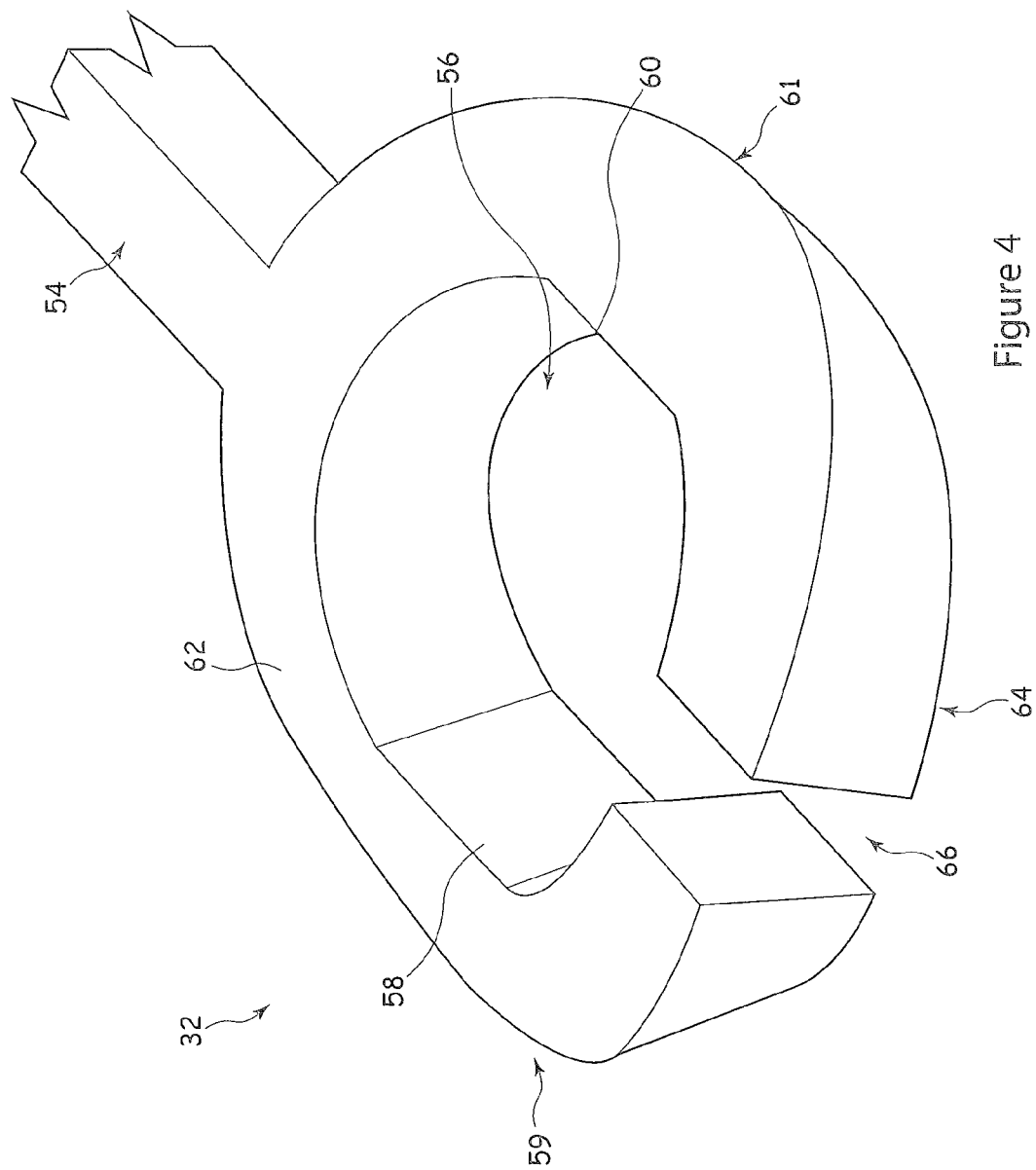
FIG. 4 is a perspective view of the preferred embodiment of second coupling element.

Referring now to FIG. 4, there is shown in perspective a view the corresponding second coupling element 32 which is formed integrally with its respective bar element 54. This is also substantially circular in plan view and curved to a curvature the same or similar to that of the enlarged head 30. The second coupling element 32 is provided with a cut-out 56 which has a shape and dimensions corresponding to those of the enlarged head 34 of the first coupling element, thus to have two side walls 58, 60 facing one another and extending towards one another from the top 62 to the bottom 64 of the second coupling element 32. These side walls 58, 60 could be said to be provided on arms 59, 61 of the second coupling element 32.

At a front end of the second coupling element 32 there is provided an aperture 66, which has a shape and dimensions corresponding to those of the bar element 52 of the first coupling element 30. As will be apparent from FIG. 4, and as shown in more detail in the following Figures, the second coupling element 32 is provided, in this embodiment, with no features to accommodate within its volume the side extending feet 48, 50 of the first coupling element. In other embodiments, there may be provided suitable recesses in the bottom wall 64 of the second coupling element 32 with shapes corresponding to the shapes of the feet 48, 50 so as to accommodate these.

Figure 5:
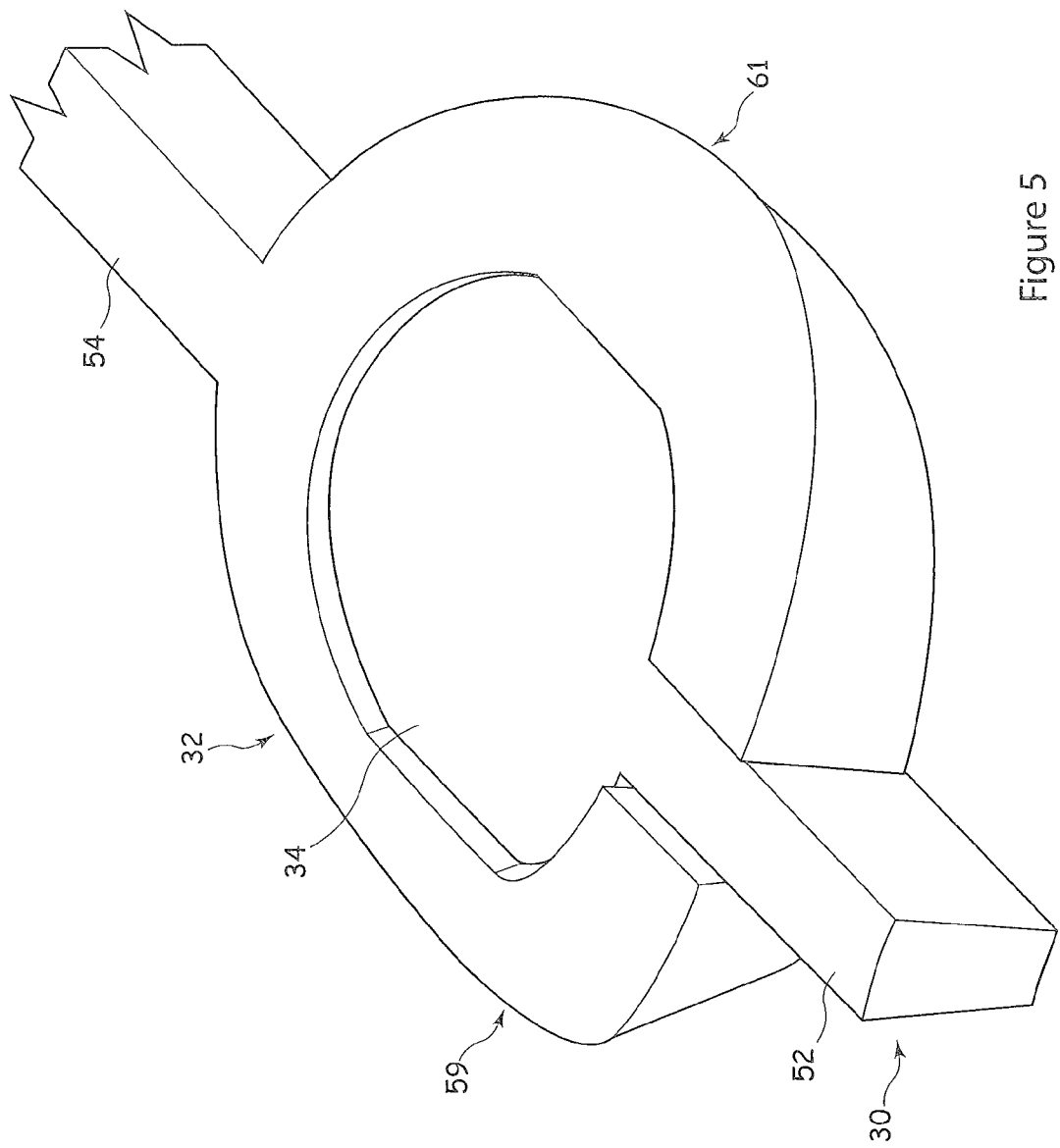
FIG. 5 is a perspective view from above of the first and second coupling elements joined together.
Figure 6:
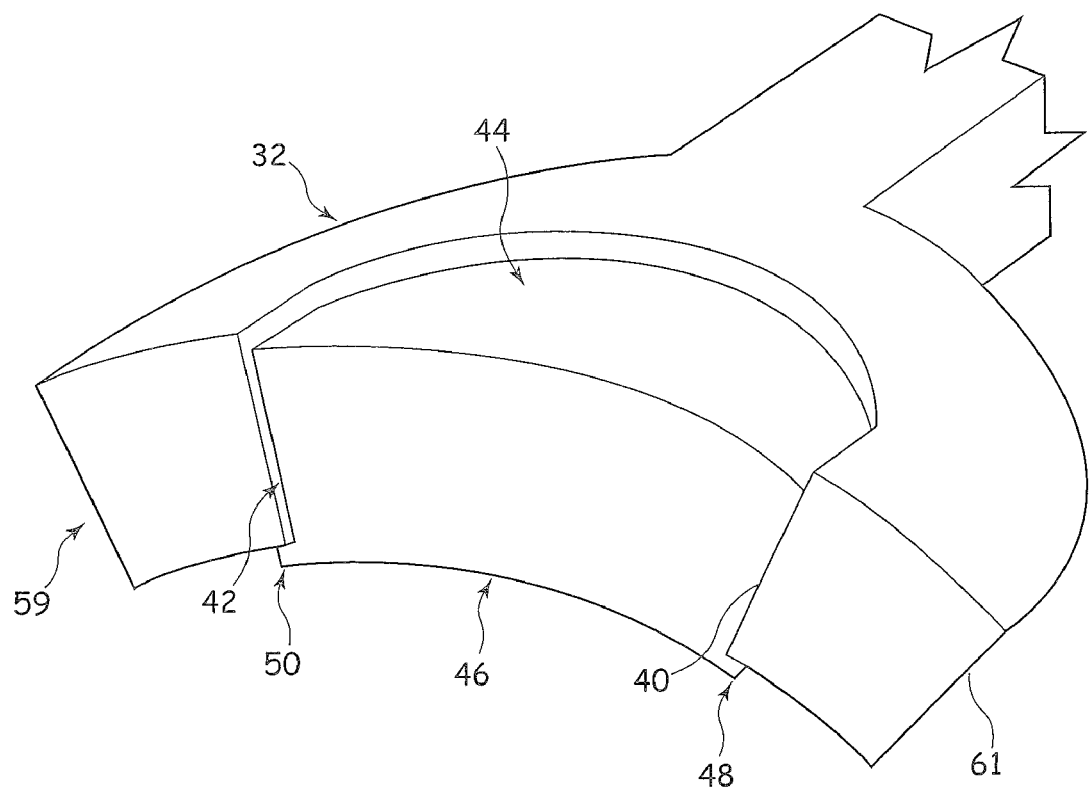
FIG. 6 is a cross-sectional view of the first and second coupling elements when joined together.

As a result of the shapes and features of the second and first coupling elements, 30 and 32, as can be seen in FIGS. 5 and 6 in particular, in this embodiment the first coupling element 30 sits just below the line of the second coupling element 32, with the side extending feet 48, 50 sitting below and abutting against the lower surface 64 of the second coupling element 32.

In practice, the first coupling element 30 is coupled to the second coupling element 32 by a snap-fit action, in which the second coupling element 32 can be sprung open so as to allow the top surface 44 of the enlarged head 34 of the first coupling element 30 to move into the second coupling element from below. The curved nature of the top surface 44 of the enlarged head 34 assists in urging apart the side arms 59, 61 of the second coupling element. As the enlarged head moves up the walls 58, 60 of the second coupling element 32, the side arms 59, 61 gradually spring back towards there rest position, in so doing maintaining close contact with the first coupling element. It is preferred that the arms 59, 61 remain slightly biased apart when the first coupling element 30 is fitted to the second coupling element 32 in order to maintain tension in the coupling between the two.

It will be apparent particularly from FIG. 6 that the tapering or wedged shaped arrangement of the side walls 40/60 and 42/58 (sidewalls 58 and 60 are shown more clearly in FIG. 4) ensures that the first coupling element 30 remains biased upwardly relative to the second coupling element 32 and that the side extending feet 48, 50 hold it in place. This provides a secure attachment of the first and second coupling elements 30, 32 irrespective of the operating condition of the stent 20, in particular whether it is compressed on an introducer or expanded into a deployed condition. Moreover, the straight side walls 40/60 and 42/58 ensure that the coupling does rotate, thus providing a coupling of these two parts which is solid and substantially immovable. This gives the bar elements 52, 54, when viewed together, characteristics equivalent to those of a conventional one-piece tie bar.

In practice, it is envisaged that the end sections 22, 26 of the stent 20 have slightly different structures compared to the intermediate stent sections 24. In particular, they need not be provided with coupling elements 30, 32 on both sides of the stent ring but only on what would be the internal side once the stent sections 22, 26 have been fitted to the assembly. There could be provided, as alluded to above, with additional end-stent features such as radiopaque markers, barbs and so on. It is not excluded, however, that the end sections 22, 26 of any stent assembly could have substantially the same form as the internal sections 24, that is being provided with coupling elements 30, 32 extending in both directions from the stent ring, with the coupling elements 30, 32 at the outer ends of the stent assembly being left unused. This would have the advantage of providing a stent structure in which all of the stent frames can be identical to one another and thus would substantially facilitate bulk manufacture and assembly.

In the particular embodiment described above, the various sections 22, 26 forming the stent assembly 20 have substantially similar characteristics in terms of their flexibilities, the expansion force they generate (in the case of a self-expanding stent structure) and so on. This is typically achieved by using struts which are substantially identical in their physical characteristics for all of the stent sections 22, 24, 26. However, it is envisaged that some embodiments could be provided with stent sections which have different characteristics, in order to give the stent different characteristics along its length. For instance, the stent assembly 20 could be provided with some stent sections which are relatively stiffer or relatively more flexible compared to the other stent sections of the assembly. In the case of more flexible stent sections, this would give the assembly greater flexibility at certain positions along the stent. For example, stent sections towards the end of the assembly could be made relatively more flexible to improve the fit of the stent within a lumen of a patient and also to reduce trauma to the vessel wall at the ends of the stent. Different characteristics of stent rings can be achieved in any suitable manner, for example by using thicker or thinner material for the stent sections, by differentially heat treating the material with the stent sections (in particular in connection with stent sections made of shape memory material) and so on.

The stent assembly 20 could have any desired length, achieved by coupling together the appropriate number of stent sections 22, 24, 26.

Thus, the characteristics of the stent assembly 20 can easily be optimised in terms of length for the particular medical application, as well as optimised in terms of its physical characteristics by selection of stent sections of the appropriate characteristics (flexibility, stiffness and so on). The arrangement thus provides for a stent which can be produced easily, quickly and with characteristics which are optimal for a particular medical application, without any substantial increase in manufacture or development costs as would be the case of prior art stent structures.

Figure 7A:
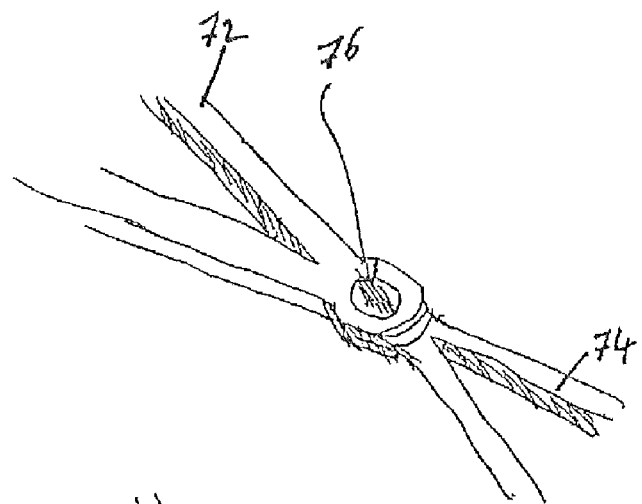
FIGS. 7a to 7c show another embodiment of stent coupling arrangement.
Figure 7B:
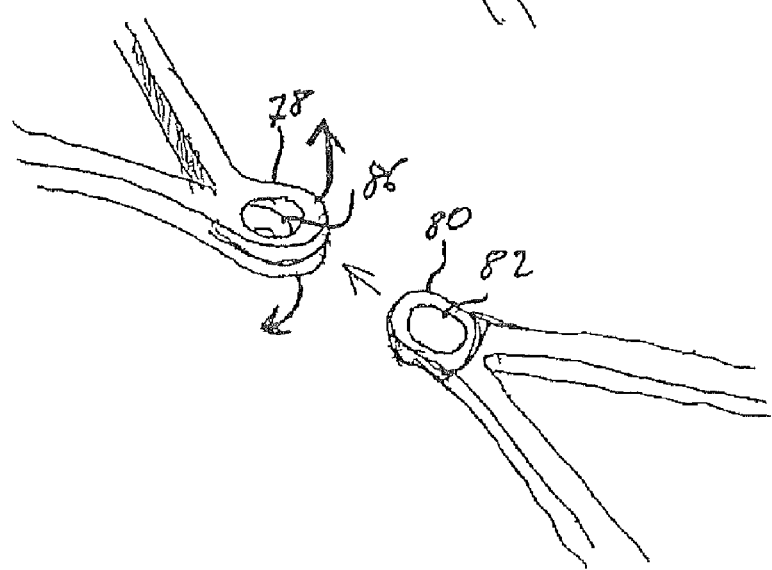
Figure 7C:
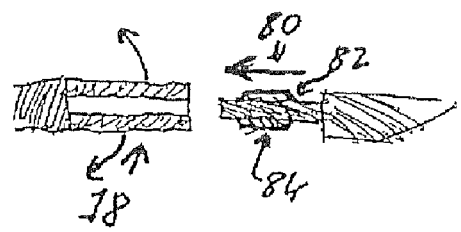

Referring now to FIGS. 7a to 7c, there is shown another embodiment of the coupling element structure for coupling two stent rings to one another. In this embodiment, the first and second coupling elements 78, 80 are located at the apices of respective stent rings 72, 74, such that the entirety of the coupling between the stent rings 72, 74 is provided by the coupling elements themselves without there being any tie-bar element there between. Of course, the coupling elements 78, 80 could be located at the ends of two tie-bar sections in a manner similar to the embodiment shown in FIGS. 2 to 6 above.

In this embodiment, the second coupling element 78 has a form of what could be described as a jaw-like arrangement which clips over the first element 80, the latter being provided with upper and lower bosses 82, 84 which fit to corresponding apertures or recesses 86 in the jaws of the second coupling element 78. It will be appreciated that the raised elements or bosses 82, 84 will have shapes which correspond with the shapes of the recesses or apertures 86. In FIGS. 7a and 7b, these shapes are shown as being substantially oval, although they could have shapes analogous to the first and second coupling elements of the embodiment FIGS. 2 to 6. With a more rounded shape, it is envisaged that a suitable contact adhesive or cement 76 could be provided to fix the first and second coupling elements 78, 80 to one another.

Figure 8A:
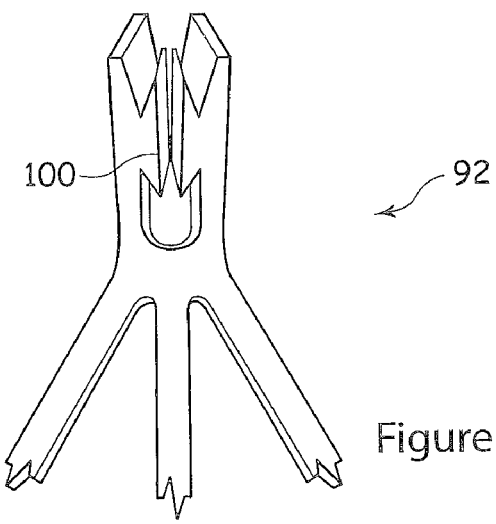
FIGS. 8a to 8c show another embodiment of stent coupling arrangement.
Figure 8B:
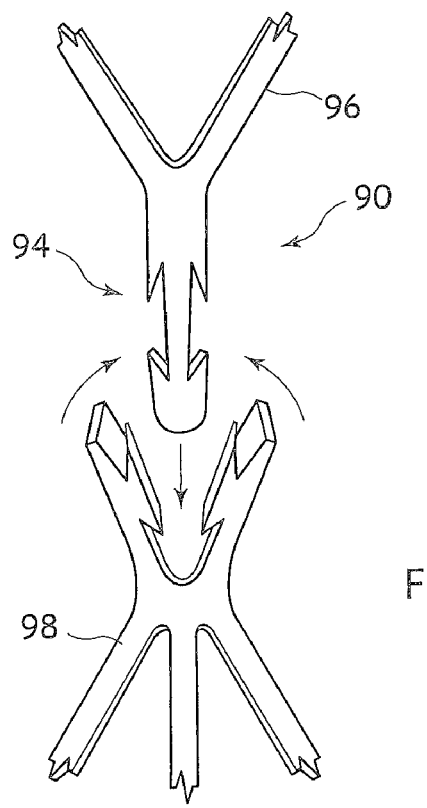
Figure 8C:
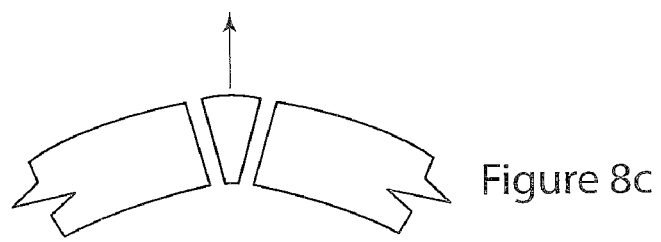

Referring now to FIGS. 8a to 8c, there is shown another embodiment of coupling arrangement 90 provided on respective stent rings 96, 98. The arrangement 90 includes a jaw-like coupling element 92 which is provided on its internal walls with the two jaws or latches 100 having a fish-tail shape. The second coupling element 94 includes corresponding fish-tail shaped recesses which are able to snap into the jaw elements 92 so that the fish-tails 100 are caught in the recesses of the element 94. For this purpose, there may be provided some flexibility of the coupling elements 92, 94 to ensure that these connect together as desired. Of course, the use of a biasing force to bias the jaws of the jaw element 92 closed will assist in this process.

Referring to FIG. 8c, there is shown a cross-sectional view, in longitudinal section, of the coupling arrangement 90, in which the element 94 is shown to have a wedge shape that fits into corresponding shape of the jaw elements 92. This shape is not dissimilar from that of the coupling elements 30/32 of the embodiment of FIGS. 2 to 6 although it is, in this instance, provided without side extending feet 48/50. The coupling elements remain in place for the reason that the stent rings 96, 98 would in practice expand to substantially the same amounts and, in the case of self-expanding stent elements, will continue to bias the stent rings against the lumen wall. This will have the effect that the coupling element 94 cannot drift out of the jaws 92 in the radial direction of the stent rings. Of course, if desired, side extending feet such as the feet 48/50 of the embodiments of FIGS. 2 to 6 could be provided.

What is claimed is:

1. A stent assembly able to be conformed into a plurality of configurations including a compressed and an expanded configuration, the stent assembly including a plurality of stent sections, each stent section being provided with at least one set of coupling elements, wherein the coupling elements of at least two of said stent sections have co-operating forms with substantially flat side walls and a snap fit coupling, said coupling elements co-operating to lock together in a substantially fixed manner such that the coupling elements lock together so as to be substantially immovable relative to one another in all assembled configurations of the stent assembly,
wherein the coupling elements comprise a first coupling element which has a generally round head and a corresponding second coupling element;
wherein the substantially flat side walls taper towards one another in a radially internal direction of the stent section carrying the first coupling element, and
wherein an innermost side of the first coupling element section is provided with side extending flanges or feet.

2. A stent assembly according to claim 1, wherein the generally rounded head is curved in a circumferential direction of the stent section.

3. A stent assembly according to claim 2, wherein the generally rounded head has a radial curvature which substantially matches a radial curvature of the stent assembly when deployed.

4. A stent assembly according to claim 1, wherein at least one of said stent sections has different performance characteristics compared to the other stent section or sections of said stent assembly.

5. A stent assembly according to claim 1, wherein the stent sections have substantially similar performance characteristics include with respect to one or more of: compressibility, flexibility, expansion force.

6. An implantable medical device including the stent assembly according to claim 1.

7. An implantable medical device according to claim 6, wherein the device is one of: a stent, a stent graft, an occlusion device, a vena cava filter.

8. A kit including plurality of stent sections for forming a stent assembly, wherein the stent sections are able to be conformed into a plurality of configurations including a compressed and an expanded configuration, each stent section being provided with at least one set of coupling elements, wherein the coupling elements of at least two of said stent sections have cooperating forms with substantially flat side walls and a snap fit coupling, said coupling elements co-operating to lock together in a substantially fixed manner such that the coupling elements lock together so as to be substantially immovable relative to one another in all assembled configurations of the stent assembly,
wherein the coupling elements comprise a first coupling element which has a generally round head and a corresponding second coupling element;
wherein the substantially flat side walls taper towards one another in a radially internal direction of the stent section carrying the first coupling element, and
wherein an innermost side of the first coupling element section is provided with side extending flanges or feet.

9. A kit according to claim 8, wherein the stent sections are identical to one another.

10. A kit according to claim 8, including one or more end stent sections.

11. An implantable medical device including the stent assembly formed from the kit according to claim 8.

12. An implantable medical device according to claim 11, wherein the device is one of: a stent, a stent graft, an occlusion device, a vena cava filter.

13. A method of forming an implantable medical device from a kit wherein the device is one of: a stent, a stent graft, an occlusion device, a vena cava filter provided with a stent assembly able to be conformed into a plurality of configurations including a compressed and an expanded configuration, the stent assembly including a plurality of stent sections, each stent section being provided with at least one set of coupling elements, wherein the coupling elements of at least two of said stent sections have co-operating forms with substantially flat side walls and a snap fit coupling, said coupling elements co-operating to lock together in a substantially fixed manner such that the coupling is solid and substantially immovable in all assembled configurations of the stent assembly; the method including the steps of snap-fitting together the plurality of stent sections to form a stented structure, said snap-fitting providing a coupling in which the coupling elements lock together so as to be substantially immovable relative to one another in all assembled configurations of the stent assembly, wherein the coupling elements comprise a first coupling element which has a generally round head and a corresponding second coupling element;

wherein the substantially flat side walls taper towards one another in a radially internal direction of the stent section carrying the first coupling element, and wherein an innermost side of the first coupling element section is provided with side extending flanges or feet.

\* \* \* \* \*